United States Patent
Parthasaradhi Reddy et al.

(10) Patent No.: US 9,115,118 B2
(45) Date of Patent: Aug. 25, 2015

(54) PROCESS FOR THE RESOLUTION OF OMEPRAZOLE

(71) Applicant: HETERO RESEARCH FOUNDATION, Hyderabad, Andhrapradesh (IN)

(72) Inventors: Bandi Parthasaradhi Reddy, Hyderabad (IN); Kura Rathnakar Reddy, Hyderabad (IN); Rapolu Raji Reddy, Hyderabad (IN); Dasari Muralidhara Reddy, Hyderabad (IN); Bandi Vamsi Krishna, Hyderabad (IN); Voggu Ramesh Reddy, Hyderabad (IN)

(73) Assignee: Hetero Research Foundation (IN)

( * ) Notice: Subject to any disclaimer, the term of this patent is extended or adjusted under 35 U.S.C. 154(b) by 0 days.

(21) Appl. No.: 14/264,450

(22) Filed: Apr. 29, 2014

(65) Prior Publication Data

US 2014/0235859 A1    Aug. 21, 2014

Related U.S. Application Data

(62) Division of application No. 13/504,224, filed as application No. PCT/IN2009/000634 on Nov. 12, 2009, now Pat. No. 8,748,619.

(51) Int. Cl.
*C07D 401/14* (2006.01)
*C07D 401/12* (2006.01)

(52) U.S. Cl.
CPC ............ *C07D 401/12* (2013.01); *C07D 401/14* (2013.01)

(58) Field of Classification Search
CPC .................................................... C07D 401/14
USPC ................................ 546/194, 273.7; 544/360
See application file for complete search history.

(56) References Cited

U.S. PATENT DOCUMENTS 7,345,061 B2 * 3/2008 Dahlstrom ..................... 514/338

* cited by examiner

*Primary Examiner* — Patricia L Morris
(74) *Attorney, Agent, or Firm* — Caesar Rivise, PC

(57) ABSTRACT

The present invention relates to process for the resolution of omeprazole. The present invention further provides a novel compound of enantiomers of omeprazole cyclic amine salt and a process for preparing it. The present invention also provides a solid of (R)- or (S)-omeprazole cyclic amine salt and a process for preparing it. The present invention also provides a process for the preparation of esomeprazole magnesium dehydrate substantially free of its trihydrate form. The present invention also provides a process for the preparation of recovery of chiral BINOL.

1 Claim, No Drawings

PROCESS FOR THE RESOLUTION OF OMEPRAZOLE

FIELD OF THE INVENTION

The present invention relates to process for the resolution of omeprazole. The present invention further provides a novel compound of enantiomers of omeprazole cyclic amine salt and a process for preparing it. The present invention also provides a solid of (R)- or (S)-omeprazole cyclic amine salt and a process for preparing it. The present invention also provides a process for the preparation of esomeprazole magnesium dihydrate substantially free of its trihydrate form. The present invention also provides a process for the preparation of recovery of chiral BINOL.

BACKGROUND OF THE INVENTION

Omeprazole, chemically 5-methoxy-2-[[(4-methoxy-3,5-dimethyl-2-pyridinyl)methyl]sulfinyl]-1H-benzimidazole and its therapeutic uses were disclosed in European Patent No. 5129. Omeprazole is a well-known gastric acid secretion inhibitor, and is useful as an anti ulcer agent. Omeprazole has a stereogenic center at sulfur and therefore exist as two optical isomers such as R-omeprazole and S-omeprazole (esomeprazole).

The alkaline salts of (S)-enantiomer of omeprazole (esomeprazole), the pharmaceutical preparations of these salts and the method of treatment of gastric acid-related diseases using them were disclosed in U.S. Pat. Nos. 4,738,974, 5,877,192 and 5,714,504. The U.S. Pat. Nos. 4,738,974, 5,877,192 and 5,714,504 are incorporated herein by reference.

These compounds and structurally related compounds have a stereogenic center at sulfur and therefore exist as two optical isomers. The resolution processes of racemates of these compounds were, for example, disclosed in DE 4035455 and WO 94/27988. According to these processes chiral ether such as fenchyloxymethyl or chiral acyloxy methyl group such as mandeloyl— is introduced into the 1-position of benzimidazole ring of racemic sulfoxide compound to obtain a diastereomeric mixture, diastereomers are then separated and desired isomer is liberated from a separated diastereomer. The process requires either the preparation of fenchyloxymethyl chloride and then reaction with the racemic compound; or introduction of chloromethyl group on 1-position of benzimidazole ring, followed by reaction with the chiral auxiliary. We found that these intermediates are difficult to prepare and involve in many steps.

PCT Publication No. WO 94/27988 disclosed certain salts (sodium, magnesium, lithium, potassium, calcium and alkyl ammonium salts) of single enantiomers of omeprazole and processes for their preparation thereof. These compounds have improved pharmacokinetic and metabolic properties which will give an improved therapeutic profile such as a lower degree of interindividual variation.

PCT Publication No. WO 96/02535 disclosed a process for the preparation of the single enantiomers of omeprazole and structurally related compounds as well as salts thereof.

PCT Publication No. WO 97/02261 disclosed a process for the optical purification of certain enantiomerically enriched benzimidazole derivatives by using a crystallization method.

PCT Publication Nos. WO 2008/004245, WO 2006/094904, WO 2007/013743, CN 1087739 and CN 1223262 disclosed processes for preparation of an optically pure or optically enriched enantiomer of a sulphoxide compound using R— or S-1,1'-bi-2-naphthol (R— or S-BINOL).

The resolution of sulfoxide compounds including racemic omeprazole were described in PCT Publication No. WO 2004/002982. The method requires expensive reagents like titanium compounds, two chiral reagents namely diethyl-D-tartarate and L-Mandelic acid.

Enantioselective synthesis was described for example in Euro. J. Biochem. 166 (1987) 453 and U.S. Pat. No. 5,948,789. Disadvantages of these methods are that strict control of conditions is to be maintained and strict control of quantities of oxidizing agents is required for avoiding oxidation of desired sulfoxide to sulfone impurity. Moreover, these methods require expensive reagents like titanium isoproxide and diethyl-D-tartarate.

U.S. Pat. No. 7,176,319 B2 disclosed a resolution of racemic sulfoxide compounds using chiral camphoursulfonyl chloride.

U.S. Pat. Nos. 5,948,789 and 7,365,206 B2 disclosed stereoselective oxidation methods for the preparation of chiral substituted 2-(2-pyridinylmethylsulfinyl)-1H-benzimidazoles.

PCT Publication No. WO 2007/074099 disclosed process for the preparation of optiacally pure benzimidazole derivatives by inclusion complex with (S)-1,1,2-triphenyl-1,2-ethanediol.

Resolution of omeprazole with chiral 1,1'-binaphtyl-2-2'-diyl hydrogen (BNPPA) was disclosed in co-pending Application No. PCT/1N2009/000567.

PCT Publication No. WO 2008/092939 disclosed a process for the preparation of substantially optically pure omeprazole with the formation of a complex by using chiral amine or chiral quaternary ammonium salt. Magnesium salt of esomeprazole trihydrate was disclosed in PCT Publication No. WO 98/54171. Barium salt of esomeprazole was disclosed in PCT Publication No. WO 2004/099181.

U.S. Patent Application No. 2005/0182099 disclosed tert-butylammonium salts of omeprazole and esomeprazole.

U.S. Patent Application No. 2007/0004778 disclosed adamantan ammonium salt of omeprazole and esomeprazole. Esomeprazole arginine salt was disclosed in PCT Publication No. WO 2007/071444.

PCT Publication No. WO 2009/047775 disclosed a process for the preparation of high assayed esomeprazole magnesium dihydrate substantially free of its trihydrate form from esomeprazole or esomeprazole sodium and also disclosed crystalline form 1, form 2 and amorphous form of esomeprazole calcium salt.

One object of the present invention is to provide a novel process for the resolution of omeprazole.

Another object of the present invention is to provide a novel compound of enantiomers of omeprazole cyclic amine salt and a process for preparing it.

Another object of the present invention is to provide a solid of (R)- or (S)-omeprazole cyclic amine salt and a process for preparing it.

Another object of the present invention is to provide a process for the preparation of esomeprazole magnesium dihydrate substantially free of its trihydrate form.

Still another object of the present invention is to provide a process for the preparation of recovery of chiral BINOL.

SUMMARY OF THE INVENTION

In one aspect of the present invention there is provided a novel process for the resolution of omeprazole, which comprises:

a) reacting 5-methoxy-2-[[(4-methoxy-3,5-dimethyl-2-pyridinyl)methyl]sulfinyl]-1H-benzimidazole (omeprazole) with a chiral 1,1'-bi-2-naphthol (chiral BINOL) in presence of aromatic solvent to obtain corresponding diastereomer complexes;
b) isolating preferentially one diastereomer complex from the mixture of diastereomer complexes;
c) reacting isolated diastereomer complex with a cyclic amine in presence of a solvent or a mixture solvents to obtain (R)- or (S)-omeprazole cyclic amine salt; and
d) optionally, converting (R)- or (S)-omeprazole cyclic amine salt to the corresponding omeprazole enantiomer or a salt thereof.

In another aspect of the present invention there is provided a novel compound of enantiomers of omeprazole cyclic amine salt of formula I:

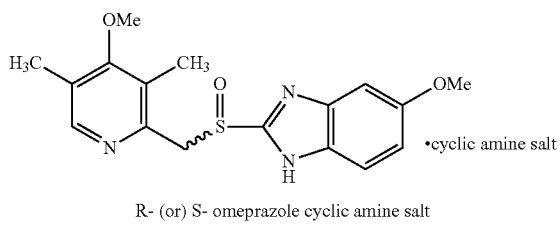

R- (or) S- omeprazole cyclic amine salt

In another aspect of the present invention there is provided a process for the preparation of enantiomers of omeprazole cyclic amine salt of formula I, which comprises reacting (R)- or (S)-omeprazole or a mixtures thereof with a cyclic amine to obtain the corresponding enantiomers of omeprazole cyclic amine salt of formula I.

In another aspect of the present invention there is provided a solid of (R)- or (S)-omeprazole cyclic amine salt.

In another aspect of the present invention there is provided a process for the preparation of solid of (R)- or (S)-omeprazole cyclic amine salt, which comprises:
a) reacting (R)- or (S)-omeprazole or a mixtures thereof with a cyclic amine to obtain (R)- or (S)-omeprazole cyclic amine salt; and
b) crystallizing (R)- or (S)-omeprazole cyclic amine salt from solvent or mixture of solvents selected from acetone, ethylaceate and isopropyl acetate.

In another aspect of the present invention there is provided a process for the preparation of esomeprazole magnesium dihydrate substantially free of its trihydrate form, which comprises:
a) adding esomeprazole cyclic amine salt to a solution of magnesium ion source in an alcoholic solvent;
b) stirring the mass obtained in step (a);
c) distilling off the alcoholic solvent from the solution;
d) dissolving the residue obtained in step (c) in a chlorinated solvent;
e) filtering the solution formed in step (d);
f) distilling off the chlorinated solvent from the solution obtained in step (e);
g) dissolving the residue obtained in step (f) in a solvent system comprising acetone and water wherein content of water is 2-6 moles per mole of esomeprazole cyclic amine salt used in step (a); and
h) precipitating esomeprazole magnesium dihydrate substantially free of its trihydrate form from the solution obtained in step (g) by adding acetone as an anti-solvent.

Yet another aspect of the present invention there is provided a process for the preparation of recovery of chiral BINOL, which comprises:
a) reacting R-omeprazole-chiral BINOL complex with base;
b) separating the R-omeprazole and chiral BINOL as free compound or as their salts from the reaction mass obtained in step (a); and
c) recovering chiral BINOL.

DETAILED DESCRIPTION OF THE INVENTION

According to one aspect of the present invention, there is provided a novel process for the resolution of omeprazole, which comprises:
a) reacting 5-methoxy-2-[[(4-methoxy-3,5-dimethyl-2-pyridinyl)methyl]sulfinyl]-1H-benzimidazole (omeprazole) with a chiral 1,1'-bi-2-naphthol (chiral BINOL) in presence of aromatic solvent to obtain corresponding diastereomer complexes;
b) isolating preferentially one diastereomer complex from the mixture of diastereomer complexes;
c) reacting isolated diastereomer complex with a cyclic amine in presence of a solvent or a mixture solvents to obtain (R)- or (S)-omeprazole cyclic amine salt; and
d) optionally, converting (R)- or (S)-omeprazole cyclic amine salt to the corresponding omeprazole enantiomer or a salt thereof.

The aromatic solvent used in step (a) may be selected from toluene, xylene, benzene, styrene and aromatic solvent may alone or in combination with aliphatic hydrocarbon solvent such as cyclohexane, hexane and heptanes may be used. Preferably the aromatic solvent is toluene.

The diastereomer complexes formed in step (a) are then separated. It is well known that diastereomer complexes differ in their properties such as solubility and they can be separated based on the differences in their properties. The separation of the diastereomer complexes can be performed using the methods known to the person skilled in the art. These methods include chromatographic techniques and fractional crystallization, preferable method being fractional crystallization.

Crystallization of preferentially one diastereomer complex from the solution of diastereomer complexes can be performed by conventional methods such as cooling, partial removal of solvents, seeding or a combination thereof. Fractional crystallization may also occur from the solution under condition of diasteromeric complex formation. Isolation can be repeated until the desired chiral purity is obtained. But, usually one or two isolations may be sufficient. The separated solid may be collected by the method known such as centrifugation or filtration.

The cyclic amine used in step (c) is five or six member cyclic amine salts. Preferably the five and six member cyclic amine salts is selected from piperidine, pyrrolidine and piperazine, and more preferably the six member cyclic amine salt is piperidine.

The term "solvent" may used to refer to a single solvent or a mixture of solvents.

Preferable solvent used in step (c) is selected from acetone, ethyl acetate, methyl acetate and isopropyl acetate and, more preferable solvent is acetone.

(R)- or (S)-omeprazole cyclic amine salt formed in step (c) is converted into omeprazole enantiomer or salt of omeprazole enantiomer in step (d) by the methods such as by adding an acid or a source of a cation.

Preferable salt of omeprazole enantiomer in step (d) is sodium, potassium or magnesium salt of omeprazole enantiomer.

According to another aspect of the present invention, there is provided a novel compound of enantiomers of omeprazole cyclic amine salt of formula I:

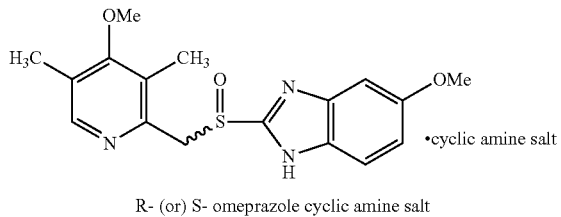

R- (or) S- omeprazole cyclic amine salt

The cyclic amine salt is five or six member cyclic amine salts. Preferably the five and six member cyclic amine salts is selected from piperidine, pyrrolidine and piperazine.

Preferred compounds of formula I are the compounds of formula II(a)-II(c) as shown below:

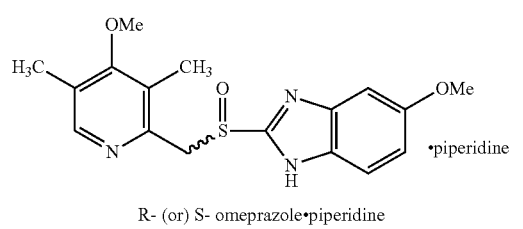

R- (or) S- omeprazole•piperidine

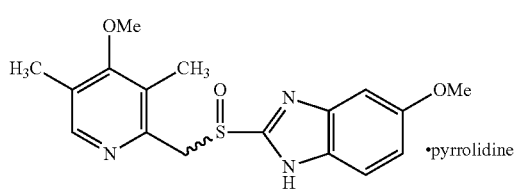

R- (or) S- omeprazole•pyrrolidine

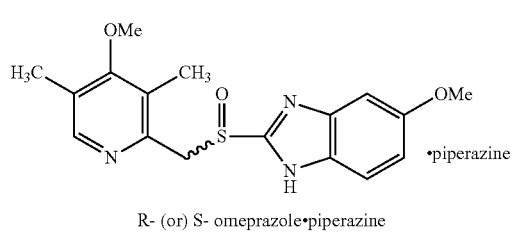

R- (or) S- omeprazole•piperazine

According to another aspect of the present invention, there is provided a process for the preparation of enantiomers of omeprazole cyclic amine salt of formula I, which comprises reacting (R)- or (S)-omeprazole or a mixtures thereof with a cyclic amine to obtain the corresponding enantiomers of omeprazole cyclic amine salt of formula I.

The cyclic amine is five or six member cyclic amine salts. Preferably the five and six member cyclic amine salts is selected from piperidine, pyrrolidine and piperazine, and more preferably the six member cyclic amine salt is piperidine.

According to another aspect of the present invention, there is provided a solid of (R)- or (S)-omeprazole cyclic amine salt. Preferable solid is crystalline.

The cyclic amine salt of (R)- or (S)-omeprazole is five or six member cyclic amine salts. Preferably the five and six member cyclic amine salts is selected from piperidine, pyrrolidine and piperazine, and more preferably the six member cyclic amine salt is piperidine.

According to another aspect of the present invention, there is provided a process for the preparation of solid of (R)- or (S)-omeprazole cyclic amine salt, which comprises:

a) reacting (R)- or (S)-omeprazole or a mixtures thereof with a cyclic amine to obtain (R)- or (S)-omeprazole cyclic amine salt; and b) crystallizing (R)- or (S)-omeprazole cyclic amine salt from solvent or mixture of solvents selected from acetone, ethyl acetate and isopropyl acetate.

The cyclic amine used in step (a) is five or six member cyclic amine salts. Preferably the five and six member cyclic amine salts is selected from piperidine, pyrrolidine and piperazine, and more preferably the six member cyclic amine salt is piperidine.

According to another aspect of the present invention, there is provided a process for the preparation of esomeprazole magnesium dihydrate substantially free of its trihydrate form, which comprises:

a) adding esomeprazole cyclic amine salt to a solution of magnesium ion source in an alcoholic solvent;

b) stirring the mass obtained in step (a);

c) distilling off the alcoholic solvent from the solution;

d) dissolving the residue obtained in step (c) in a chlorinated solvent;

e) filtering the solution formed in step (d);

f) distilling off the chlorinated solvent from the solution obtained in step (e);

g) dissolving the residue obtained in step (f) in a solvent system comprising acetone and water wherein content of water is 2-6 moles per mole of esomeprazole cyclic amine salt used in step (a); and h) precipitating esomeprazole magnesium dihydrate substantially free of its trihydrate form from the solution obtained in step (g) by adding acetone as an anti-solvent.

The water content of the esomeprazole magnesium dihydrate is between 4.0 and 6.7% by weight, and typically between 4.5 and 5.5% by weight.

The term "esomeprazole magnesium dihydrate substantially free of trihydrate form" refers to the esomeprazole magnesium dihydrate containing less than about 5% trihydrate form of esomeprazole magnesium by weight, preferably less than about 2% trihydrate form of esomeprazole magnesium by weight, more preferably less than about 1% trihydrate form of esomeprazole magnesium by weight, and still more preferably essentially free of trihydrate form of esomeprazole magnesium. "Essentially free of trihydrate form of esomeprazole magnesium" means that no trihydrate form of esomeprazole magnesium.

The cyclic amine salt of esomeprazole used as starting material is five or six member cyclic amine salts. Preferably the five and six member cyclic amine salts is selected from piperidine, pyrrolidine and piperazine, and more preferably the six member cyclic amine salt is piperidine.

The esomeprazole cyclic amine salt in step (a) is added to the solution of magnesium ion source in an alcoholic solvent at a temperature below 60° C., more preferably added at a temperature between 0° C. and 45° C. and still more preferably added at a temperature between 15° C. and 40° C.

Preferable magnesium ion source used in step (a) is magnesium chloride, magnesium sulfate or magnesium alkoxide such as magnesium methoxide or magnesium ethoxide, and more preferable magnesium ion source is magnesium chloride.

Preferable alcoholic solvent used in step (a) is methanol or ethanol, and more preferable alcoholic solvent is methanol.

The reaction mass in step (b) is preferably stirred at least for about 15 minutes, more preferably stirred at least for about 20 minutes and still more preferably stirred for about 20 minutes to 1 hour.

The reaction mass in step (b) is preferably stirred at a temperature below 50° C., more preferably stirred at a temperature between 0° C. and 45° C. and still more preferably stirred at a temperature between 15° C. and 40° C.

The distillation of the alcoholic solvent in step (c) is preferably carried out under vacuum at a temperature below 55° C., more preferably carried out under vacuum at a temperature below 50° C. and still more preferably carried out under vacuum at a temperature between 30° C.-45° C.

The residue in step (d) is preferably dissolved in the chlorinated solvent at a temperature below 60° C., more preferably dissolved at a temperature between 0° C. and 45° C. and still more preferably dissolved at a temperature between 15° C. and 40° C.

Preferable chlorinated solvent used in step (d) is methylene dichloride or chloroform and more preferable chlorinated solvent is methylene dichloride.

The distillation of the chlorinated solvent in step (f) is preferably carried out under vacuum at a temperature below 55° C., more preferably carried out under vacuum at a temperature below 50° C. and still more preferably carried out under vacuum at a temperature between 30° C.-45° C.

The residue in step (g) is preferably dissolved in the solvent system comprising acetone and water at a temperature below 60° C., more preferably dissolved at a temperature between 0° C. and 45° C. and still more preferably dissolved at a temperature between 15° C. and 40° C.

Preferably the content of water in the solvent system comprising methanol and water in step (g) is 2.5-5.5 moles per mole of esomeprazole cyclic amine salt used in step (a), and more preferably the content of water is 3-5 moles per mole of esomeprazole cyclic amine salt used in step (a).

The precipitated esomeprazole magnesium dihydrate substantially free of its trihydrate form in step (h) is collected by conventional methods such as filtration or centrifugation.

According to another aspect of the present invention, there is provided a process for the preparation of recovery of chiral BINOL, which comprises:
a) reacting R-omeprazole-chiral BINOL complex with base;
b) separating the R-omeprazole and chiral BINOL as free compound or as their salts from the reaction mass obtained in step (a); and
c) recovering chiral BINOL.

The base used in step (a) may be inorganic or organic base or a mixture thereof. Preferably the base may be selected from potassium hydroxide, sodium hydroxide, calcium hydroxide, magnesium hydroxide, piperidine, pyrrolidine and piperazine. More preferably the base is selected from potassium hydroxide, sodium hydroxide, calcium hydroxide, magnesium hydroxide and piperidine.

The following examples are given for the purpose of illustrating the present invention and should not be considered as limitations on the scope or spirit of the invention.

EXAMPLES

Example 1

Preparation of Esomeprazole-S-BINOL Complex

S-1,1'-bi-2-naphthol (124 gm) was added to a solution of 5-methoxy-2-[(3,5-dimethyl-4-methoxy-2-pyridyl)methylsulfinyl]-1H-benzimidazole (100 gm) (Omeprazole) in toluene (1200 ml) at room temperature. The reaction mixture was heated to 50 to 55° C. for 1 hour and then the solution was cooled to room temperature. The solid obtained was collected by filtration, washed with toluene, and then dried at 45 to 50° C. under vacuum for 4 hours to obtain 72 gm of esomeprazole-S-BINOL complex.

Example 2

Preparation of Esomeprazole-S-BINOL Complex

S-1,1'-bi-2-naphthol (124 gm) was added to a solution of omeprazole (100 gm) in a mixture of toluene and cyclohexane (2000 ml, 4:1) at room temperature. The reaction mixture was heated to 50 to 55° C. and maintained for 1 hour at 50 to 55° C. The solution was cooled to room temperature and filtered, washed with a mixture of toluene and cyclohexane (200 ml, 4:1). The solid was dried at 45 to 50° C. under vacuum for 4 hours to obtain 80 gm of esomeprazole-S-BINOL complex.

Example 3

Preparation of Esomeprazole

A mixture of piperidine (33 gm), isopropyl acetate (400 ml) and water (400 ml) was added to esomeprazole-S-BINOL complex (80 gm) as obtained in example 2 at room temperature. The reaction mixture was stirred for 35 minutes at room temperature and the layers were separated. To the organic layer was added piperidine (16 gm) and water (150 ml). The contents were stirred for 35 minutes at room temperature and the layers were separated. The total aqueous layer was washed with isopropyl acetate (150 ml). The combined isopropyl acetate layer may be used for recovery of S-BINOL. To the aqueous layer was added methylene dichloride (400 ml), stirred for 15 minutes. The pH was adjusted to 7.2 to 7.3 with 10% hydrochloric acid for 15 minutes and the layers were separated. The aqueous layer was extracted with methylene dichloride (100 ml) and distilled off the solvent under vacuum to obtain 44 gm of esomeprazole as a residual oil.

Example 4

Preparation of Esomeprazole Piperidine Salt

To esomeprazole (44 gm) as obtained in example 3 was added acetone (220 ml) and piperidine (14 gm) at room temperature. The reaction mixture was stirred for 1 hour at room temperature and the solid was separated. The separated solid was cooled to 10 to 15° C. and maintained for 1 hour at 10 to 15° C. The solid obtained was collected by filtration, washed with chilled acetone and, then dried at 40 to 45° C. under vacuum to obtain 40 gm of esomeprazole piperidine salt.

Example 5

Preparation of Esomeprazole Piperidine Salt

To esomeprazole-S-BINOL (80 gm) as obtained in example 1 was added acetone (400 ml) and piperidine (27 gm) at room temperature and the contents were heated to 40 to 45° C. for 1 hour. The reaction mass was cooled to room temperature and stirred for 30 minutes. The reaction mass further cooled to 5 to 10° C. and maintained for 2 hours at 5 to 10° C., filtered. The solid obtained was washed with chilled acetone and the solid dried at 40 to 45° C. under vacuum to obtain 38 gm of esomeprazole piperidine salt.

Example 6

Preparation of Esomeprazole Magnesium Dihydrate
To a mixture of esomeprazole piperidine salt (38 gm) as obtained in example 4, acetone (209 ml) and water (5 ml) were added at room temperature and the contents were stirred for 30 minutes at room temperature. To the reaction mass was added the solution of anhydrous magnesium chloride (4 gm) in methanol (68 ml) at room temperature. The solution obtained was stirred for 2 hours at room temperature and filtered, washed with acetone and, then dried at 40 to 45° C. under vacuum to obtain 28 gm of esomeprazole magnesium dihydrate.

Example 7

Preparation of Esomeprazole Magnesium Dihydrate
Esomeprazole piperidine salt (20 gm) was dissolved in methanol (100 ml) at room temperature. To the solution was added a hot solution of anhydrous magnesium chloride (3 gm) in methanol (40 ml) at room temperature. The reaction mass was maintained for 1 hour at room temperature and distilled off the solvent completely under vacuum at 40° C. to obtain a residue. To the residue was added isopropyl alcohol (100 ml) and stirred for 15 minutes at room temperature. To the solution obtained was added acetone (40 ml) and the contents were maintained for 2 hours at room temperature. The separated solid was filtered, washed with acetone and, the solid was dried at 40 to 45° C. under vacuum to obtain 14 gm of esomeprazole magnesium dihydrate.

Example 8

Preparation of Esomeprazole Magnesium Dihydrate
To a mixture of esomeprazole-S-BINOL complex (80 gm), acetone (240 ml) and water (8 ml) was added piperidine (13 gm) and then slowly heated to 40 to 45° C. for 1 hour to obtain clear solution. The solution was cooled to 30° C. To the solution was added a hot solution of magnesium chloride (7 gm) in methanol (80 ml) at 30° C. and maintained for 1 hour at 30 to 35° C. Again maintained the reaction mass for 1 hour at 25 to 28° C. and filtered. The solid obtained was washed with a mixture of acetone and methanol (40 ml; 3:1) and dried the solid at 40 to 45° C. under vacuum to obtain 26 gm of esomeprazole magnesium dihydrate.

Example 9

Preparation of Esomeprazole Magnesium Dihydrate
To the esomeprazole (42 gm) as obtained in example 3 was added acetone (280 ml) and piperidine (10 gm) at room temperature. The reaction mixture was stirred for 1 hour at 40 to 45° C., cooled to 30° C. and then added water (7 ml) under string. The reaction mass was added to a hot solution of magnesium chloride (6 gm) in methanol (93 ml) at 30° C. and maintained for 2 hour at 27 to 30° C. The solid obtained was collected by filtration, washed with a mixture of acetone and methanol (30 ml, 3:1) and, then dried at 40 to 45° C. under vacuum to obtain 30 gm of esomeprazole magnesium dihydrate.

Example 10

Preparation of Esomeprazole Pyrrolidine Salt
To esomeprazole (20 gm) was added acetone (100 ml) and pyrrolidine (7 gm) at room temperature. The reaction mixture was stirred for 1 hour at room temperature and the solid was separated. The separated solid was cooled to 10 to 15° C. and maintained for 1 hour at 10 to 15° C. The solid obtained was collected by filtration, washed with chilled acetone and then dried at 40 to 45° C. under vacuum to obtain 16 gm of esomeprazole pyrrolidine salt.

Example 11

Preparation of Esomeprazole Piperazine Salt
Esomeprazole (28 gm) was added to acetone (140 ml) and piperazine (8 gm) at room temperature. The reaction mixture was stirred for 1 hour at room temperature and the solid was separated. The separated solid was cooled to 10 to 15° C. and maintained for 1 hour at 10 to 15° C., filtered. The solid obtained was washed with chilled acetone and dried at 40 to 45° C. under vacuum to obtain 23 gm of esomeprazole piperazine salt.

Example 14

Preparation of Esomeprazole Magnesium Dihydrate
A mixture of piperidine (33 gm), isopropyl acetate (400 ml) and water (400 ml) was added to esomeprazole-S-BINOL complex (80 gm) as obtained in example 2 at room temperature. The reaction mixture was stirred for 35 minutes at room temperature and the layers were separated. To the organic layer was added piperidine (16 gm) and water (150 ml). The contents were stirred for 35 minutes at room temperature and the layers were separated. The total aqueous layer was washed with isopropyl acetate (150 ml) and methylene dichloride (400 ml) was added to reaction mass, stirred for 15 minutes. The pH was adjusted to 7.2 to 7.3 with 10% hydrochloric acid for 15 minutes and the layers were separated. The aqueous layer was extracted with methylene dichloride (100 ml). The methylene dichloride layer was added piperidine (12 gm) and stirred for 1 hour at room temperature. Distilled of solvent completely and co-distilled with methanol to obtain residue. To the residue was added methanol (370 ml) and stirred for 30 minutes at room temperature. A solution of anhydrous magnesium chloride (6 gm) in methanol (92 ml) was added to the warming solution at 30° C., stirred for 40 minutes at 30° C., filtered on hy-flow bed and washed with methanol. The obtained reaction mass was distilled off completely under vacuum at below 40° C. to obtain residue. To the residue was added methylene chloride (1150 ml) and stirred for 10 minutes. The reaction mass was filtered on hy-flow bed, the filtrate is distilled off completely under vacuum and co-distilled with methanol. To the residue was added methanol (69 ml) and stirred for 10 minutes. To the reaction mixture was added water (7 ml) and acetone (243 ml) and stirred for 1 hour at room temperature. The reaction mass was cooled to 0 to 5° C. and maintained for 1 hour at 0 to 5° C., filtered. The solid obtained was washed with acetone and dried the solid at 40 to 45° C. under vacuum for to obtain 20 gm of esomeprazole magnesium dihydrate.

Example 15

Preparation of Esomeprazole Magnesium Dihydrate

Esomeprazole piperidine salt (15 gm) was added to a solution of anhydrous magnesium chloride (2 gm) in methanol (150 ml) for 10 minutes at 25 to 30° C. and then stirred for 30 minutes at 25 to 30° C. Distilled off methanol completely under vacuum at below 40° C. and then co-distilled two times with methylene dichloride (each time 150 ml). To the residue was added methylene dichloride (750 ml) and anhydrous sodium sulphate (30 gm) at 25 to 30° C., the contents were stirred for 15 minutes, the resulting mass was passed on hi-flow and washed the bed with methylene dichloride (150 ml). The resulting filtrate was distilled under vacuum at below 40° C. and then co-distilled with methanol (75 ml). To the resulting residue was added acetone (135 ml) and water (3 ml), stirred for 15 minutes at 25 to 30° C. and then distilled under vacuum at below 40° C. until the mass volume reaches to 30 ml. To the resulting mass was added acetone (60 ml) slowly at 35 to 40° C., stirred for 10 minutes, and again added acetone (60 ml), stirred for 10 minutes and then cooled to 25° C. The mass was stirred for 2 hours at 20 to 25° C., further cooled down to 5° C. and stirred for 30 minutes at 5 to 10° C. Filtered the material, washed with acetone (15 ml) and then dried at 45 to 50° C. for 5 hours to give 7.9 gm of esomeprazole magnesium dihydrate.

Example 16

Recovery of S-BINOL

To the mother liquor (filtrate) obtained after filtration in example 1 was added methanol (600 ml) and potassium hydroxide (24 gm) at room temperature and maintained for 5 hours at room temperature. The reaction mass was again maintained for 1 hour at 10 to 15° C. and then filtrated. The filtrate was distilled off completely under vacuum at 45° C. To the solid obtained was added water (800 ml) and stirred for 30 minutes. The pH was adjusted to 8.5 to 9.0 with 10% hydrochloric acid solution and then maintained for 1 hour at room temperature. The solid was collected by filtration, washed with water, and then dried the solid at 50 to 55° C. under vacuum to obtain 75 gm of S-BINOL (HPLC Purity: 80% S-BINOL, 17% R-omeprazole, 2.6% esomeprazole).

Example 17

Recovery of S-BINOL

To the mother liquor (filtrate) obtained after filtration in example 1 was added acetone (600 ml) and piperadine (40 gm) at room temperature and maintained for 5 hours at room temperature. The reaction mass was again maintained for 1 hour at 10 to 15° C. and then filtered. The filtrate was distilled off completely under vacuum at 45° C. To the solid obtained was added water (800 ml) and stirred for 30 minutes. The pH was adjusted to 8.5 to 9.0 with 10% hydrochloric acid solution and then maintained for 1 hour at room temperature. The solid was collected by filtration, washed with water, and then dried the solid at 50 to 55° C. under vacuum to obtain 70 gm of S-BINOL (HPLC Purity: 80% S-BINOL, 18% R-omeprazole, 1.7% esomeprazole).

Example 18

Recovery of S-BINOL

Isopropyl acetate layer as obtained in example 3 was distilled off to obtain a residue. To the residue was added water (400 ml) and the pH was adjusted to 8.5 to 9.0 with 10% hydrochloric acid solution and then maintained for 1 hour at room temperature. The solid obtained was collected by filtration, washed with water, and then dried the solid at 50 to 55° C. under vacuum to obtain 35 gm of S-BINOL (HPLC Purity: 80% S-BINOL, 1.6% R-omeprazole, 18% esomeprazole).

We claim:

1. A compound of the enantiomers of omeprazole cyclic amine salt of formula I:

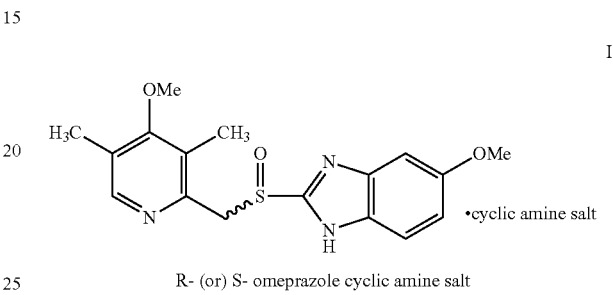

R- (or) S- omeprazole cyclic amine salt wherein the cyclic amine salt is a five or six membered cyclic amine salt, further wherein the compound is selected from compounds of formula II(a) to II(c):

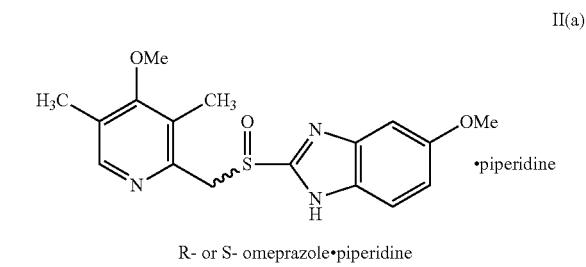

R- or S- omeprazole•piperidine

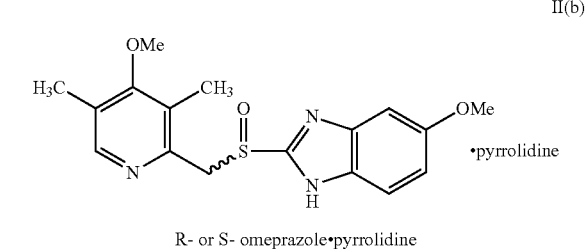

R- or S- omeprazole•pyrrolidine

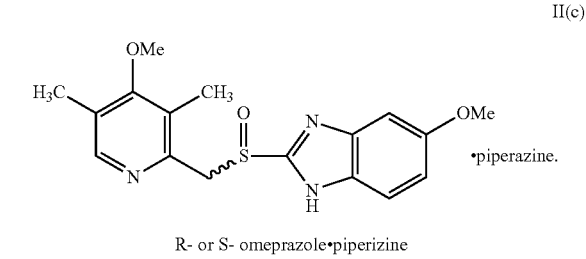

R- or S- omeprazole•piperizine

* * * * *